United States Patent
Ouyang et al.

(10) Patent No.: US 10,219,728 B2
(45) Date of Patent: *Mar. 5, 2019

(54) ANALYTE MONITORING: STABILIZER FOR SUBCUTANEOUS GLUCOSE SENSOR WITH INCORPORATED ANTIGLYCOLYTIC AGENT

(71) Applicant: Abbott Diabetes Care Inc., Alameda, CA (US)

(72) Inventors: Tianmei Ouyang, Fremont, CA (US); Zenghe Liu, Alameda, CA (US); Hyun Cho, Berkeley, CA (US); Benjamin J. Feldman, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 953 days.

This patent is subject to a terminal disclaimer.

(21) Appl. No.: 14/445,750

(22) Filed: Jul. 29, 2014

(65) Prior Publication Data
US 2014/0336486 A1 Nov. 13, 2014

Related U.S. Application Data

(63) Continuation of application No. 13/437,681, filed on Apr. 2, 2012, now Pat. No. 8,792,956, which is a (Continued)

(51) Int. Cl.
*A61B 5/1486* (2006.01)
*A61B 5/145* (2006.01)
(Continued)

(52) U.S. Cl.
CPC ........ *A61B 5/14532* (2013.01); *A61B 5/1473* (2013.01); *A61B 5/1477* (2013.01); *A61B 5/14865* (2013.01); *A61B 5/0031* (2013.01)

(58) Field of Classification Search
CPC .................................................. A61B 5/14532
See application file for complete search history.

(56) References Cited

U.S. PATENT DOCUMENTS

| 4,245,634 A | 1/1981 | Albisser et al. |
| 4,467,811 A | 8/1984 | Clark, Jr. |

(Continued)

FOREIGN PATENT DOCUMENTS

| JP | S 62-261341 | 11/1987 |
| JP | 10-221221 | 8/1998 |

(Continued)

OTHER PUBLICATIONS

Ricardo et al. "Borate minerals stabilize ribose." Science. Jan. 9, 2004;303(5655)196.*

(Continued)

*Primary Examiner* — Meredith Weare
(74) *Attorney, Agent, or Firm* — Vorys, Sater, Seymour and Pease LLP

(57) ABSTRACT

An analyte sensor including an antiglycolytic agent or a precursor thereof and a chelating agent that stabilizes the antiglycolytic agent positioned proximate to the working electrode of the sensor. Also provided are systems and methods of using the electrochemical analyte sensors in analyte monitoring.

19 Claims, 11 Drawing Sheets

Related U.S. Application Data continuation of application No. 12/167,820, filed on Jul. 3, 2008, now Pat. No. 8,160,670, which is a continuation-in-part of application No. 11/322,165, filed on Dec. 28, 2005, now Pat. No. 8,515,518.

(51) Int. Cl.
 *A61B 5/1473* (2006.01)
 *A61B 5/1477* (2006.01)
 *A61B 5/00* (2006.01)

(56) References Cited

U.S. PATENT DOCUMENTS

| | | |
|---|---|---|
| 4,527,240 A | 7/1985 | Kvitash |
| 5,171,689 A | 12/1992 | Kawaguri et al. |
| 5,204,267 A * | 4/1993 | Sangha .................. C12Q 1/54 436/14 |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |
| 5,379,238 A | 1/1995 | Stark |
| 5,387,327 A | 2/1995 | Khan |
| 5,445,920 A | 8/1995 | Saito |
| 5,514,718 A | 5/1996 | Lewis et al. |
| 5,593,852 A | 1/1997 | Heller et al. |
| 5,665,222 A | 9/1997 | Heller et al. |
| 5,791,344 A | 8/1998 | Schulman et al. |
| 5,955,371 A | 9/1999 | Ikeda et al. |
| 5,965,380 A | 10/1999 | Heller et al. |
| 5,971,922 A | 10/1999 | Arita et al. |
| 5,972,199 A | 10/1999 | Heller et al. |
| 6,049,727 A | 4/2000 | Crothall |
| 6,083,710 A | 7/2000 | Heller et al. |
| 6,091,976 A | 7/2000 | Pfeiffer et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,212,416 B1 | 4/2001 | Ward et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,295,506 B1 | 9/2001 | Heinonen et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,475,750 B1 | 11/2002 | Han et al. |
| 6,514,718 B2 | 2/2003 | Heller et al. |
| 6,551,494 B1 | 4/2003 | Heller et al. |
| 6,558,321 B1 | 5/2003 | Burd et al. |
| 6,560,471 B1 | 5/2003 | Heller et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,605,200 B1 | 8/2003 | Mao et al. |
| 6,605,201 B1 | 8/2003 | Mao et al. |
| 6,632,844 B1 | 10/2003 | Landt |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,694,191 B2 | 2/2004 | Starkweather et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,773,564 B1 | 8/2004 | Yugawa et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,833,490 B1 | 12/2004 | Goddijn et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,931,327 B2 | 8/2005 | Goode, Jr. et al. |
| 6,932,894 B2 | 8/2005 | Mao et al. |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,990,366 B2 | 1/2006 | Say et al. |
| 6,998,247 B2 | 2/2006 | Monfre et al. |
| 7,003,341 B2 | 2/2006 | Say et al. |
| 7,024,245 B2 | 4/2006 | Lebel et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,192,450 B2 | 3/2007 | Brauker et al. |
| 7,226,978 B2 | 6/2007 | Tapsak et al. |
| 7,276,029 B2 | 10/2007 | Goode, Jr. et al. |
| 7,299,082 B2 | 11/2007 | Feldman et al. |
| 7,310,544 B2 | 12/2007 | Brister et al. |
| 7,335,294 B2 | 2/2008 | Heller et al. |
| 8,160,670 B2 * | 4/2012 | Ouyang .............. A61B 5/14532 204/403.01 |
| 8,515,518 B2 * | 8/2013 | Ouyang .............. A61B 5/14865 600/345 |
| 8,792,956 B2 * | 7/2014 | Ouyang .............. A61B 5/14532 600/345 |
| 2002/0019022 A1 | 2/2002 | Dunn et al. |
| 2002/0042090 A1 | 4/2002 | Heller et al. |
| 2002/0161288 A1 | 10/2002 | Shin et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0045783 A1 | 3/2003 | March et al. |
| 2003/0065308 A1 | 4/2003 | Lebel et al. |
| 2003/0134347 A1 | 7/2003 | Heller et al. |
| 2003/0146110 A1 | 8/2003 | Karinka et al. |
| 2003/0168338 A1 | 9/2003 | Gao et al. |
| 2003/0176933 A1 | 9/2003 | Lebel et al. |
| 2003/0187338 A1 * | 10/2003 | Say .................... A61M 5/1723 600/345 |
| 2003/0217966 A1 | 11/2003 | Tapsak et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0106858 A1 | 6/2004 | Say et al. |
| 2004/0106860 A1 * | 6/2004 | Say .................... A61B 5/14532 600/345 |
| 2004/0133164 A1 | 7/2004 | Funderburk et al. |
| 2004/0138588 A1 | 7/2004 | Saikley et al. |
| 2004/0167801 A1 | 8/2004 | Say et al. |
| 2004/0171921 A1 | 9/2004 | Say et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0225338 A1 | 11/2004 | Lebel et al. |
| 2004/0236200 A1 | 11/2004 | Say et al. |

(56) References Cited

U.S. PATENT DOCUMENTS

| | | |
|---|---|---|
| 2004/0247603 A1 | 12/2004 | Sabbadini |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0032743 A1 | 2/2005 | Miljkovic |
| 2005/0033132 A1 | 2/2005 | Shults et al. |
| 2005/0043598 A1 | 2/2005 | Goode, Jr. et al. |
| 2005/0090607 A1 | 4/2005 | Tapsak et al. |
| 2005/0107677 A1 | 5/2005 | Ward et al. |
| 2005/0112169 A1 | 5/2005 | Brauker et al. |
| 2005/0121322 A1 | 6/2005 | Say et al. |
| 2005/0143635 A1 | 6/2005 | Kamath et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0287620 A1 | 12/2005 | Heller et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0166629 A1 | 7/2006 | Reggiardo |
| 2006/0173444 A1 | 8/2006 | Choy et al. |
| 2006/0222566 A1 | 10/2006 | Brauker et al. |
| 2006/0229512 A1 | 10/2006 | Petisce et al. |
| 2006/0247508 A1 | 11/2006 | Fennell |
| 2007/0016381 A1* | 1/2007 | Kamath ............. A61B 5/14532 702/19 |
| 2007/0149875 A1* | 6/2007 | Ouyang ............. A61B 5/14532 600/347 |
| 2007/0163880 A1 | 7/2007 | Woo et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033268 A1* | 2/2008 | Stafford ............. A61B 5/14503 600/345 |
| 2008/0319296 A1 | 12/2008 | Bernstein et al. |

FOREIGN PATENT DOCUMENTS

| | | |
|---|---|---|
| JP | 2001-510382 | 7/2001 |
| JP | 2005-517181 | 6/2005 |
| JP | 2009-522023 | 6/2009 |
| WO | 02/103343 | 12/2002 |
| WO | 2005/033698 | 4/2005 |

OTHER PUBLICATIONS

Ricardo et al., "Borate Minerals Stabilize Ribose" Science 303:196 (2004).

* cited by examiner

ANALYTE MONITORING: STABILIZER FOR SUBCUTANEOUS GLUCOSE SENSOR WITH INCORPORATED ANTIGLYCOLYTIC AGENT

CROSS-REFERENCE TO RELATED APPLICATIONS

This application is a continuation of U.S. patent application Ser. No. 13/437,681, filed on Apr. 2, 2012, which is a continuation of U.S. patent application Ser. No. 12/167,820, filed on Jul. 3, 2008, now U.S. Pat. No. 8,160,670, which is a continuation-in-part, and claims the benefit of priority of U.S. patent application Ser. No. 11/322,165, filed Dec. 28, 2005, now U.S. Pat. No. 8,515,518, which are incorporated herein by reference.

BACKGROUND

The monitoring of the level of glucose or other analytes, such as lactate or oxygen, in certain individuals is vitally important to their health. High or low levels of glucose or other analytes may have detrimental effects. For example, the monitoring of glucose is particularly important to individuals with diabetes, as they must determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using calorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test. In addition, some individuals wish to avoid the pain associated with the test. These situations may result in hyperglycemic or hypoglycemic episodes. An in vivo glucose sensor that continuously or automatically monitors the individual's glucose level would enable individuals to more easily monitor their glucose, or other analyte levels.

Analyte monitoring devices have been developed for continuous or automatic monitoring of analytes, such as glucose, in the blood stream or interstitial fluid. Such devices include electrochemical sensors, at least a portion of which are operably positioned in a blood vessel or in the subcutaneous tissue of a patient.

Regardless of the type of analyte monitoring device employed, it has been observed that transient, low readings may occur for a period of time. These spurious low readings may occur during the first hours of use, or anytime thereafter. In certain embodiments, spurious low readings may occur during the night and sometimes are referred to as "night time dropouts". For example, in the context of an operably positioned continuous monitoring analyte sensor under the skin of a user, such spurious low readings may occur for a period of time following sensor positioning and/or during the first night post-positioning. In many instances, the spurious low readings resolve after a period of time. However, these transient, low readings impose constraints upon analyte monitoring during the period in which the spurious low readings are observed. Attempts to address this problem vary and include delaying reporting readings to the user until after this period of low readings passes after positioning of the sensor, or frequent calibration of the sensor—both of which are inconvenient and neither of which is desirable.

As attention to analyte monitoring continues, there is an interest in analyte monitoring protocols that do not exhibit, or at least minimize, spurious low readings, e.g., spurious readings following device placement in a user and/or thereafter such as during the night. Spurious low readings may be caused by the presence of blood clots also known as "thrombi" that form as a result of insertion of the sensor in vivo. Such clots exist in close proximity to a subcutaneous glucose sensor and have a tendency to "consume" glucose at a high rate, thereby lowering the local glucose concentration. Of particular interest are analyte monitoring compositions and protocols and that are capable of substantially immediate and accurate analyte reporting to the user so that spurious low readings, or frequent calibrations, are minimized or are non existent.

The present invention addresses these needs.

SUMMARY OF THE INVENTION

Embodiments of the invention include electrochemical analyte sensors having an antiglycolytic agent or a precursor thereof and a chelating agent that stabilizes the antiglycolytic agent positioned proximate to the working electrode of the sensor. Also provided are systems and methods of using the electrochemical analyte sensors in analyte monitoring.

Other embodiments of the invention relate to methods and devices for monitoring of the level of an analyte using an in vivo or in vitro analyte sensor, e.g., continuous and/or automatic in vivo or in vitro monitoring using an analyte sensor. Embodiments of the subject invention include sensors that do not exhibit, or at least have a minimal period of time in which, spurious, low reading are observed. The subject invention may be employed to minimize or eliminate spurious low analyte readings obtained at any time during sensor use, including a period of time immediately after sensor activation (e.g., positioning of an analyte sensor in or on a patient) and/or anytime thereafter. Embodiments include sensors in which at least a portion of the sensor is adapted to be positioned beneath the skin of a user and which are adapted for providing clinically accurate analyte data substantially immediately after the sensor has been operably positioned in a patient (e.g., in the subcutaneous tissue, etc.) and/or without substantial interruption due to spurious analyte readings.

Embodiments of the subject invention include calibrateable analyte sensor devices in which the period of time when a first (or only) calibration is required, after positioning the sensor in a patient, is substantially reduced (excluding factory-set calibration) and/or the number of calibrations is reduced, e.g., to three or less calibrations, e.g., two or less calibrations, e.g., one calibration or no calibrations.

Embodiments of the subject devices include devices (e.g., analyte sensors) that include an antiglycolytic agent or precursor thereof and one or more chelating agents. Such chelating agents may include borate minerals, boric acid or an equivalent compound.

Also provided are methods of determining the concentration of an analyte in bodily fluid, where embodiments include determining the concentration of an analyte in a bodily fluid without any, or with only a minimal period of time in which spurious, low readings are observed. Embodiments include positioning an analyte sensor in a patient and determining, with clinical accuracy, the concentration of an analyte in bodily fluid substantially immediately following the operable positioning.

Embodiments of the subject methods include contacting an antiglycolytic agent or precursor thereof in combination with one or more chelating agents to an analyte determination site, and determining the concentration of an analyte at the site.

Embodiments of the subject methods include operably positioning a device (e.g., an analyte sensor) that includes an antiglycolytic agent or precursor thereof and one or more chelating agents in a patient, and determining the concentration of an analyte using the sensor.

Embodiments of the subject methods include analyte determination methods having a substantially reduced period of time when a first (or only) calibration is required (excluding factory-set calibration), after positioning the sensor in a patient, and/or the number of calibrations is reduced, e.g., to three or less calibrations, e.g., two or less calibrations, e.g., one calibration or no calibrations.

Also provided are methods of stabilizing an antiglycolytic agent with one or more chelating agents for use in an analyte biosensor.

Embodiments of the subject methods include coating an analyte sensor containing an antiglycolytic agent or precursor thereof with one or more chelating agents such as borate minerals, boric acid or an equivalent compound. In other embodiments, an analyte determination site may be contacted with an antiglycolytic agent or precursor thereof and one or more chelating agents such as borate minerals, boric acid, or an equivalent compound, prior to determining the concentration of an analyte at the site.

Also provided are methods of manufacturing an electrochemical sensor comprising an antiglycolytic agent or a precursor thereof and a chelating agent positioned proximate to the working electrode of the sensor, including, but not limited to, formulation in the sensing layer, deposition over the surface of the sensing layer, formulation in the membrane, deposition over the membrane, deposition on the surface of the sensor, such as the working electrode, and the like.

Also provided are systems and kits.

BRIEF DESCRIPTION OF THE DRAWINGS

The invention may be more completely understood in consideration of the following detailed description of various embodiments of the invention in connection with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
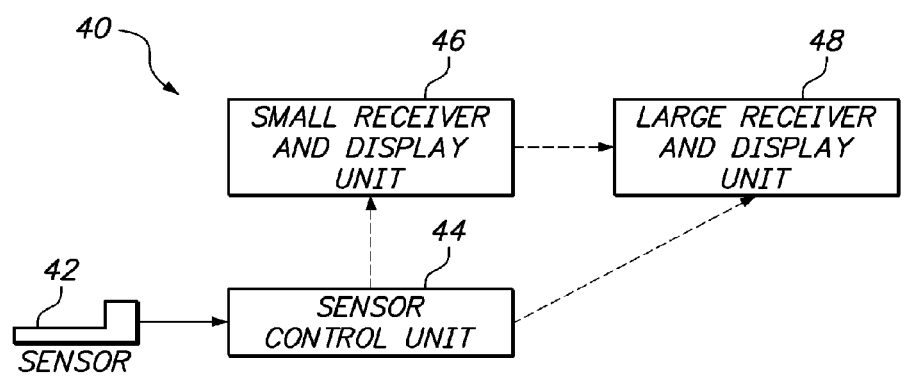
FIG. 1 shows a block diagram of an exemplary embodiment of an analyte monitor using an analyte sensor, according to the invention.

Throughout embodiments of the application, unless a contrary intention appears, the following terms refer to the indicated characteristics.

A "biological fluid" or "physiological fluid" or "bodily fluid", is any bodily fluid in which an analyte can be measured, for example, blood, interstitial fluid, dermal fluid, sweat, tears, and urine. "Blood" includes whole blood and its cell-free components, including, plasma and serum.

A "counter electrode" refers to an electrode paired with the working electrode, through which passes a current equal in magnitude and opposite in sign to the current passing through the working electrode. In the context of the invention, the term "counter electrode" is meant to include counter electrodes which also function as reference electrodes (i.e., a counter/reference electrode).

An "electrochemical sensor" is a device configured to detect the presence and/or measure the level of an analyte in a sample via electrochemical oxidation and reduction reactions on the sensor. These reactions are transduced to an electrical signal that can be correlated to an amount, concentration, or level of an analyte in the sample.

"Electrolysis" is the electrooxidation or electroreduction of a compound either directly at an electrode or via one or more electron transfer agents.

A compound is "immobilized" on a surface when it is entrapped on or chemically bound to the surface.

A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample).

Components are "immobilized" within a sensor, for example, when the components are covalently, ionically, or coordinatively bound to constituents of the sensor and/or are entrapped in a polymeric or sol-gel matrix or membrane which precludes mobility. For example, in certain embodiments an antiglycolytic agent or precursor thereof may be immobilized within a sensor.

An "electron transfer agent" is a compound that carries electrons between the analyte and the working electrode, either directly, or in cooperation with other electron transfer agents. One example of an electron transfer agent is a redox mediator.

A "working electrode" is an electrode at which the analyte (or a second compound whose level depends on the level of the analyte) is electrooxidized or electroreduced with or without the agency of an electron transfer agent.

A "working surface" is that portion of the working electrode which is coated with or is accessible to the electron transfer agent and configured for exposure to an analyte-containing fluid.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode.

A "non-corroding" conductive material includes non-metallic materials, such as carbon and conductive polymers.

When one item is indicated as being "remote" from another, this is referenced that the two items are at least in different buildings, and may be at least one mile, ten miles, or at least one hundred miles apart. When different items are indicated as being "local" to each other they are not remote from one another (for example, they can be in the same building or the same room of a building). "Communicating", "transmitting" and the like, of information reference conveying data representing information as electrical or optical signals over a suitable communication channel (for example, a private or public network, wired, optical fiber, wireless radio or satellite, or otherwise). Any communication or transmission can be between devices which are local or remote from one another. "Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless). "Receiving" something means it is obtained by any possible means, such as delivery of a physical item. When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

When two items are "associated" with one another they are provided in such a way that it is apparent that one is related to the other such as where one references the other.

Items of data are "linked" to one another in a memory when a same data input (for example, filename or directory name or search term) retrieves those items (in a same file or not) or an input of one or more of the linked items retrieves one or more of the others.

It will also be appreciated that throughout the present application, that words such as "cover", "base" "front", "back", "top", "upper", and "lower" are used in a relative sense only.

"May" refers to optionally.

When two or more items (for example, elements or processes) are referenced by an alternative "or", this indicates that either could be present separately or any combination of them could be present together except where the presence of one necessarily excludes the other or others.

Any recited method can be carried out in the order of events recited or in any other order which is logically possible. Reference to a singular item, includes the possibility that there are plural of the same item present.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

Electrochemical Analyte Sensors

Embodiments of the invention relate to electrochemical analyte sensors including an antiglycolytic agent or a precursor thereof and a chelating agent that stabilizes the antiglycolytic agent positioned proximate to the working electrode of the sensor. It has been previously shown that an antiglycolytic agent, such as L-glyceraldehyde, may be advantageously added to a biosensor to reduce the local consumption of glucose by thrombi. While this advantageously prevents spurious glucose readings, glyceraldehydes have the disadvantage of degrading over time, thereby causing further interference with glucose readings. Biosensors must be stable at various temperatures over various lengths of time since they will be subjected to a "shelf-life" prior to patient use. Embodiments of the invention demonstrate that use of a chelating agent such as borate minerals, boric acid or an equivalent compound, is capable of prevent degradation of the antiglycolytic agent, thereby stabilizing biosensors containing the antiglycolytic agents, such as L-glyceraldehyde. Accordingly, As exemplified in Reaction Scheme 1, the antiglycolytic agent L-glyceraldehyde transforms to an unstable enol under stressed condition, and decomposes rapidly to generate undescribable polymeric mixtures.

Reaction Scheme 1

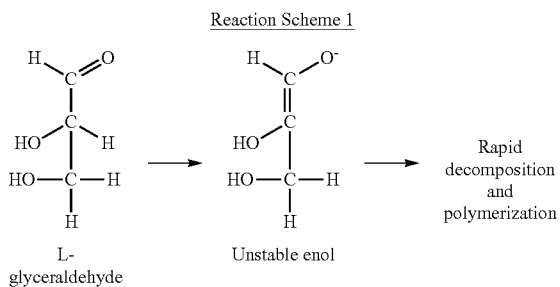 [SMILES: O=CC(O)CO ; [O-]/C=C(/O)CO]

As shown herein, the above reaction is prevented by adding a chelating agent, e.g., borate, which stabilizes the antiglycolytic agent and prevents the rapid decomposition and rapid polymerization of the antiglycolytic agent. For example, a molecule of borate and two molecules of L-glyceraldehyde will form a diglyceraldehyde borate complex, as shown below in Reaction Scheme 2, which is a stabilized complex that does not decompose and rapidly polymerized as compared to the absence of the chelating agent.

Reaction Scheme 2

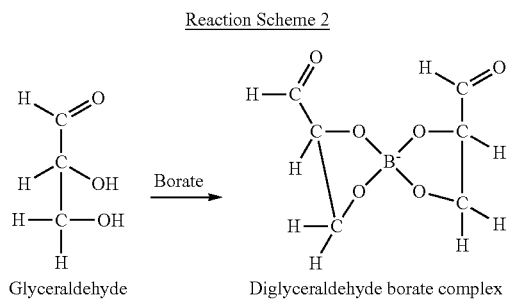 [SMILES: O=CC(O)CO ; O=CC1CO[B-]2(OCC(C=O)O2)O1]

Embodiments of the invention include devices that include an antiglycolytic agent or precursor thereof and a chelating agent that stabilizes the antiglycolytic agent or precursor thereof, e.g., analyte sensors that include an antiglycolytic agent or precursor thereof and a chelating agent.

The antiglycolytic agent or precursor thereof and the chelating agent are collectively referred to herein as "active agent".

The term "antiglycolytic" is used broadly herein to include any substance that at least retards glucose consumption of living cells. The antiglycolytic agents or antiglycolytic agent precursors may be any suitable antiglycolytic agents or precursors known or to be discovered.

Examples of antiglycolytic agents include, but are not limited to, fluorides, glyceraldehydes, mannose, glucosamine, mannoheptulose, sorbose-6-phophate, trehalose-6-phosphate, maleimide, iodoacetates, and the like, and combinations thereof. Examples of antiglycolytic agent precursors include, but are not limited to, enzymes, e.g., trehalose-6-phosphate synthase, and the like. For example, the antiglycolytic agent may be glyceraldehydes, e.g., D-glyceraldehyde, L-glyceraldehyde, or a racemic mixture of D- and L-glyceraldehyde. As noted above, fluorides may be used, e.g., sodium fluoride, potassium fluoride, etc.

Chelating agents, as used herein refer to compounds capable of forming two or more coordination bonds with organic compounds, thereby stabilizing the organic compounds from degradation and decomposition. Examples of chelating agents suitable for use in the embodiments of the invention include, but are not limited to, borate, boric acid, main group metals, such as Ca(II), and transition metals, such as, Cu (II), Zn(II), Co(II), V(IV), Mn(II), Ni(II), Fe(II), and the like. Additional chelating agents that are capable of stabilizing the organic compounds from degradation and decomposition include the Group IIIA metals, such as Al, Ga, In, and Ti.

The amount of active agent included in a sensor may vary depending on a variety of factors such as the particular active agent used, the particulars of the sensor, etc. In any event, an effective amount of active agent used—an amount sufficient to provide the requisite stabilized antiglycolytic result for the desired period of time. By way of example, in embodiments using L-glyceraldehyde as an antiglycolytic agent, the amount of L-glyceraldehyde may range from about 1 microgram to about 2 milligrams, e.g., 10 micrograms to about 200 micrograms. By way of example, in embodiments using boric acid as a chelating agent, the amount of boric acid may range from about 0.1 microgram to about 1 milligrams, e.g., 1 micrograms to about 100 micrograms. As will be appreciated by one having skill in the art, each element of the active agent may be present in equal quantities or in different quantities, depending on the specific antiglycolytic agent and chelating agent selected for use.

Embodiments of the invention are applicable to an analyte monitoring system using a sensor at least a portion of which is positioned beneath the skin of the user for the in vivo determination of a concentration of an analyte, including glucose, lactate, and the like, in a bodily fluid. The sensor may be, for example, subcutaneously positioned in a patient for the continuous or periodic monitoring an analyte in a patient's interstitial fluid. This may be used to infer the glucose level in the patient's bloodstream. The sensors of the subject invention also include in vivo analyte sensors for insertion into a vein, artery, or other portion of the body containing fluid. A sensor of the subject invention may be configured for monitoring the level of the analyte over a time period which may range from hours, days, weeks, or longer, as described in greater detail below.

Embodiments of the invention also apply to an in vitro analyte monitoring system. For example, a system in which bodily fluid is obtained and contacted with an analyte sensor above the skin. Such systems include, but are not limited to, skin opening (e.g., a laser, lancet, or the like) and sampling devices adapted to determine the concentration of an analyte in a sample of bodily fluid obtained from the skin opening, e.g., by periodically or continuously sampling fluid exuded at the site. The skin opening device and sampling device may be integrated in a single unit or otherwise. Embodiments of the invention are described primarily with respect to an analyte sensor in which at least a portion of which is operably positioned under the skin of the patient, where such description is for exemplary purposes only and is in no way intended to limit the scope of the invention in any way. It is to be understood that the subject invention may be applicable to different analyte sensors, e.g., above-skin analyte sensors.

The subject invention includes devices and methods of analyte concentration determined that have at least a substantially reduced (including completely eliminated) period of spurious, low analyte readings. In this manner, reportable analyte results may be obtained with a minimal, if any, time delay and/or interruption due to spurious low analyte readings.

Embodiments include positioning devices and systems, and methods that provide clinically accurate analyte data (e.g., relative to a reference) substantially immediately, as shown by any suitable technique known to those of skill in the art, e.g., a Clark Error Grid, Parks Error Grid, Continuous Glucose Error Grid, MARD analysis, and the like. For example, in those embodiments in which the sensor is a continuous sensor and at least a portion of the sensor is adapted to be positioned under the skin of a patient, the sensor is adapted to provide clinically accurate analyte data (e.g., relative to a reference) substantially immediately after the sensor is operably positioned in a patient. In other words, the waiting period from the time a sensor is positioned in a user and the time clinically accurate data may be obtained and used by the user, is greatly reduced relative to prior art devices that require a greater waiting period before accurate analyte data may be obtained and used by a user. By "substantially immediately" is meant from about 0 hours to less than about 5 hours, e.g., from about 0 hours to about 3 hours, e.g., from about 0 hours to less than about 1 hour, e.g., from about 30 minutes or less, where in many embodiments the sensors according to the subject invention are capable of providing clinically accurate analyte data once the sensor has been operatively positioned in the patient.

The active-agent containing devices may be analyte sensors in certain embodiments, or may be a structure that is positionable near an analyte determination site (a bodily fluid sampling site), e.g., near an analyte sensor such as near a wholly or partially implantable sensor. In certain embodiments, the structure may be a sensor insertion device, drug delivery device (e.g., insulin delivery device), etc. In certain embodiments, the active agent-containing device may be an active agent delivery device. In further describing the subject invention, the invention is described primarily with respect to an active-agent-containing analyte sensor, where such description is for exemplary purposes only and is in no way intended to limit the scope of the invention in any way. It is to be understood that an active agent may be associated with devices other than analyte sensors or otherwise contacted with an appropriate area of a patient.

In certain embodiments, the active agent may not be carried by a device, i.e. independent of the device, but rather may be otherwise applied at or substantially near the analyte determination site on the skin of a subject, such as the forearm, abdomen, and the like. Accordingly, embodiments include systems having an active agent delivery unit and an analyte sensor. In such embodiments, the active agent is formulated for transdermal delivery by a topical route, such as topical application to the skin of a subject.

The active agent employed in the subject invention may be delivered transdermally, by a topical route, formulated as applicator sticks, solutions, suspensions, emulsions, gels, creams, ointments, pastes, jellies, paints, powders, and aerosols. For example, embodiments may include an active agent in the form of a discrete patch or film or plaster or the like adapted to remain in intimate contact with the epidermis of the recipient for a period of time. For example, such transdermal patches may include a base or matrix layer, e.g., polymeric layer, in which active agent is retained. The base or matrix layer may be operably associated with a support or backing. Active agents suitable for transdermal administration may also be delivered by iontophoresis and may take the form of an optionally buffered aqueous solution that includes the active agent. Suitable formulations may include citrate or bis/tris buffer (pH 6) or ethanol/water and contain a suitable amount of active ingredient. Active agents of the subject invention may be adapted for parenteral administration, including intravenous ("IV") administration, intramuscular ("IM"), subcutaneous ("SC" or "SQ"), mucosal. The formulations for such administration may include a solution of the active agent dissolved in a pharmaceutically acceptable carrier. Among the acceptable vehicles and solvents that may be employed, include, but are not limited to, water and Ringer's solution, an isotonic sodium chloride, etc. Active agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter.

In other embodiments, the active agent may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). Methods for preparing liposomal suspensions are known in the art and thus will not be described herein in great detail.

Embodiments may also include administration of active agent using an active agent delivery device such as, but not limited to, pumps (implantable or external devices and combinations of both (e.g., certain components may be implantable and others may be external to the body such as controls for the implantable components), epidural injectors, syringes or other injection apparatus, catheter and/or reservoir operably associated with a catheter, etc. For example, in certain embodiments a delivery device employed to deliver active agent to a subject may be a pump, syringe, catheter or reservoir operably associated with a connecting device such as a catheter, tubing, or the like. Containers suitable for delivery of active agent to an active agent administration device include instruments of containment that may be used to deliver, place, attach, and/or insert the active agent into the delivery device for administration of the active agent to a subject and include, but are not limited to, vials, ampules, tubes, capsules, bottles, syringes and bags. Embodiments may also include administration of an active agent via a biodegradable implant active agent delivery device. Such may be accomplished by employing syringes to deposit such a biodegradable delivery device under the skin of a subject. The implants degrade completely, so that removal is not necessary.

Embodiments may include employing an electrode to deliver the active agent to a subject. For example, an electrode may be used that has a small port at its tip which is connected to a reservoir or pump containing an active agent. The active agent delivery electrode may be implanted using any suitable technique such as surgical cut down, laproscopy, endoscopy, percutaneous procedure, and the like. In certain embodiments a reservoir or pump may also be implanted in the subject's body. The active agent delivery electrode, or other analogous device, may be controllable such that the amount of active agent delivered, the rate at which the active agent may be delivered, and the time period over which the active agent may be delivered, etc., may be controllable and may be adjusted, e.g., by a user and/or healthcare worker.

Accordingly, embodiments include contacting an analyte determination site with an active agent or agents, and determining the concentration of an analyte, where the contacting may be by way of an analyte sensor or other structure, transdermal administration, parenteral administration, etc.

As described above, analyte sensors may include active agents. The sensors may include or incorporate active agents thereof in any suitable manner. At least a portion of the sensor (and/or other structure), e.g., a bodily fluid-contacting portion, includes active agents, and in certain embodiments substantially the entire sensor may include the active agent. Active agents may be immobilized on a surface of the sensor or may be configured to diffuse away from the sensor surface.

In certain embodiments, the active agent is a coating on at least a portion of the sensor, such as proximate to or directly on the working electrode and/or reference/counter electrode, on the sensing layer, on the flux-limiting membrane. In certain embodiments, the active agent is incorporated, e.g., embedded, or otherwise integrated into the sensor, such as the sensing layer formulation, the redox polymer formulation, the flux-limiting membrane formulation.

As will be described in greater detail below, an analyte sensor may include a matrix component such as a membrane. The membrane may be, for example, a mass transfer limiting membrane. In certain embodiments, the membrane may include the active agent such that the membrane may include a coating thereof such that the active agent may be incorporated as a thin coating positioned about a surface of the membrane, e.g., a fluid contacting surface. The amount of active agent to be included may be readily controlled by applying multiple thin coats thereof, e.g., and allowing it to dry between coats.

The thickness of a coating will be minimal so as not to appreciably increase the thickness of the membrane. In many embodiments, the thickness is substantially uniform. The thickness in certain embodiments may range from about 0.1 microns to about 100 microns, e.g., from about 1 micron to about 10 microns.

Alternatively or in addition to a coating, an active agent may be incorporated within the material of the sensor, e.g., incorporated within the material of a sensor membrane itself, the sensing layer of the working electrode, the redox polymer, the flux-limiting membrane, and the like. For example, membranes are often applied to a sensor via a spraying or dipping process, wherein the membrane material is dissolved in a solvent and the resulting solution is applied to the sensor substrate. In this case the active agent may simply be co-dissolved with the membrane material in the solvent. This results in a sensor with active agent dispersed evenly throughout the sensor membrane.

The sensors may also have the ability to emit or diffuse an active agent at a controllable rate, e.g., may include a controlled release, such as a time release, formulation. For example, a sensor (e.g., a membrane of the sensor) may include a formulation that is designed to release an active agent gradually over time, e.g., over about a period of time commensurate with a period of time in which a sensor exhibits spurious low glucose readings post-sensor insertion, e.g., about 1 hour to about 24 hours in certain embodiments. A controlled release formulation may employ a polymer or other non-antiglycolytic agent material to control the release of the active agent. The active agent release rate may be slowed by diffusion through the polymer, or the antiglycolytic agent or precursor may be released as the polymer degrades or disintegrates in the body.

The active agent may be added to the sensor during fabrication of the sensor and/or may be applied to the sensor after it has been fabricated. For example, a coating containing an active agent or agents thereof may be applied to the sensor after it has been fabricated.

Active agents may be applied to the sensor by any of a variety of methods, e.g., by spraying the active agent onto the sensor or by dipping the sensor into the active agent, by coating the active agent with a slotted die, or otherwise immersing or flooding the sensor with the active agent. In addition, the active agent may be incorporated into the sensing layer formulation, or redox polymer formulation, the flux-limiting membrane forumation.

The active agent thereof may be used with any analyte sensor, e.g., an analyte sensor configured so that at least a portion of the sensor is operably positionable under the skin of a patient for the concentration determination of an analyte. Of interest are analyte sensors that are capable of providing analyte data automatically (continuously or periodically) for about one hour or more, e.g., about a few hours or more, e.g., about a few days of more, e.g., about three or more days, e.g., about five days or more, e.g., about seven days or more, e.g., about several weeks or months.

Representative active-agent containing analyte sensors and analyte monitoring systems that include active agent containing-analyte sensors according to the subject invention are now described, where such description is for exemplary purposes only and is in no way intended to limit the scope of the invention.

Antiglycolytic Analyte Sensors and Sensor Systems

The analyte sensors and analyte monitoring systems of the embodiments of the invention may be utilized under a variety of conditions. The particular configuration of an antiglycolytic and chelating agent stabilizer sensor and other units used in an analyte monitoring system may depend on the use for which the sensor and system are intended and the conditions under which the sensor and system will operate. As noted above, embodiments include a sensor configured for implantation into a patient or user. The term "implantation" is meant broadly to include wholly implantable sensors and sensors in which only a portion of which is implantable under the skin and a portion of which resides above the skin, e.g., for contact to a transmitter, receiver, transceiver, processor, etc. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be desired, in some cases, to limit the depth of implantation of the sensor. Sensors may also be implanted in other regions of the body to determine analyte levels in other fluids. Examples of suitable sensors for use in the analyte monitoring systems of the invention are described in U.S. Pat. Nos. 6,134,461 and 6,175,752.

An exemplary embodiment of an analyte monitoring system 40 for use with an implantable antiglycolytic sensor 42, e.g., for use with a subcutaneously implantable antiglycolytic sensor, is illustrated in block diagram form in FIG. 1. Said analyte monitoring system may optionally include borate minerals or boric acid or any precursor thereof. The analyte monitoring system 40 includes, at minimum, a sensor 42 that includes an antiglycolytic agent or precursor thereof, a portion of the sensor which is configured for implantation (e.g., subcutaneous, venous, or arterial implantation) into a patient, and a sensor control unit 44. The antiglycolytic sensor 42 is coupleable to the sensor control unit 44 which may be attachable to the skin of a patient. The sensor control unit 44 operates the sensor 42, including, for example, providing a voltage across the electrodes of the sensor 42 and collecting signals from the sensor 42.

The sensor control unit 44 may evaluate the signals from the sensor 42 and/or transmit the signals to one or more optional receiver/display units 46, 48 for evaluation. The sensor control unit 44 and/or the receiver/display units 46, 48 may display or otherwise communicate the current level of the analyte. Furthermore, the sensor control unit 44 and/or the receiver/display units 46, 48 may indicate to the patient, via, for example, an audible, visual, or other sensory-stimulating alarm, when the level of the analyte is at or near a threshold level. In some embodiments, an electrical shock may be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

Antiglycolytic/Antiglycolytic Precursor-Containing Sensors

Figure 2:
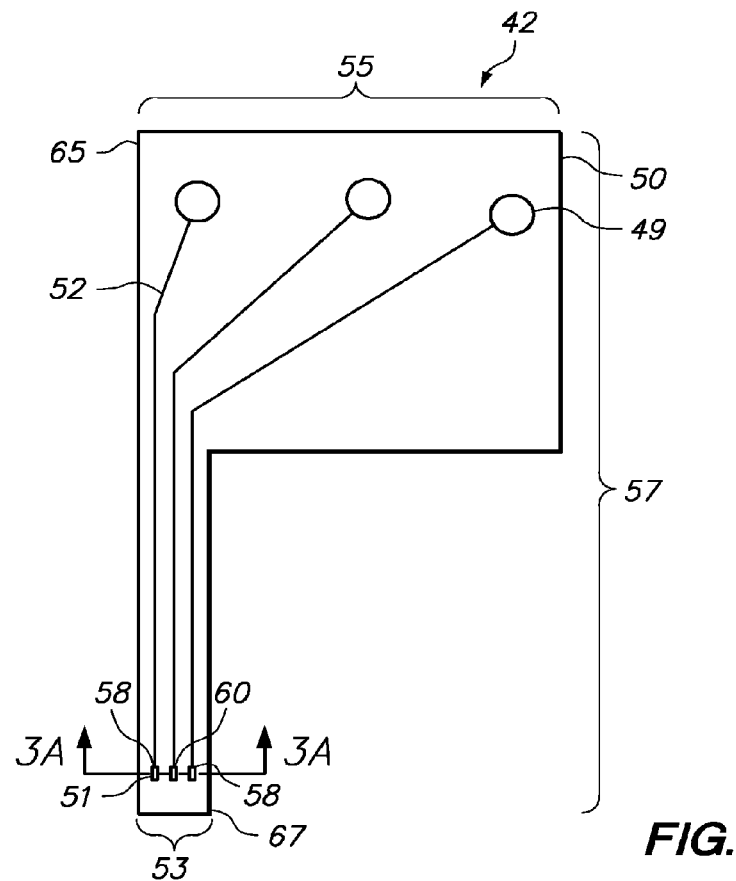
FIG. 2 is a top view of one embodiment of an analyte sensor, according to the invention.

The sensor 42 includes an antiglycolytic agent or precursor thereof and a chelating agent, including boric acid or borate minerals, as described herein, and includes at least one working electrode 58 and a substrate 50, as shown for example in FIG. 2. The sensor 42 may also include at least one counter electrode 60 (or counter/reference electrode) and/or at least one reference electrode 62 (see for example FIG. 7). The counter electrode 60 and/or reference electrode 62 may be formed on the substrate 50 or may be separate units. For example, the counter electrode and/or reference electrode may be formed on a second substrate which is also implantable in the patient or, for some embodiments of the sensors the counter electrode and/or reference electrode may be placed on the skin of the patient with the working electrode or electrodes being implanted into the patient. The use of an on-the-skin counter electrode and/or reference electrode with an implantable working electrode is described in, e.g., U.S. Pat. No. 5,593,852.

The working electrode or electrodes 58 are formed using conductive materials 52. The counter electrode 60 and/or reference electrode 62, as well as other optional portions of the sensor 42, such as a temperature probe 66 (see for example FIG. 7), may also be formed using conductive material 52. The conductive material 52 may be formed over a smooth surface of the substrate 50 or within channels 54 formed by, for example, embossing, indenting or otherwise creating a depression in the substrate 50.

Figure 4A:
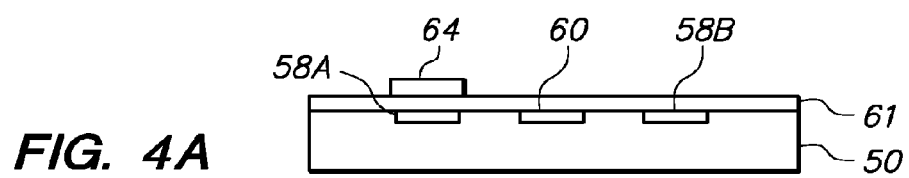
FIG. 4A is a cross-sectional view of another embodiment of an analyte sensor, according to the invention.
Figure 4B:
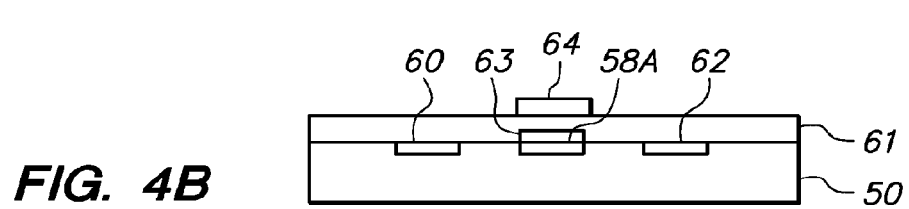
FIG. 4B is a cross-sectional view of a fourth embodiment of another embodiment of a sensor, according to the invention.
Figure 5:
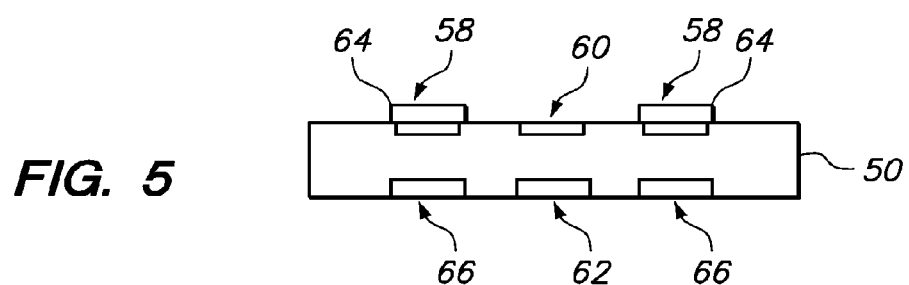
FIG. 5 is a cross-sectional view of another embodiment of an analyte sensor, according to the invention.

A sensing layer 64 (see for example FIGS. 3 and 4 and 5) may be provided proximate to or on at least one of the working electrodes 58 to facilitate the electrochemical detection of the analyte and the determination of its level in the sample fluid, particularly if the analyte can not be electrolyzed at a desired rate and/or with a desired specificity on a bare electrode. The sensing layer 64 may include an electron transfer agent to transfer electrons directly or indirectly between the analyte and the working electrode 58. The sensing layer 64 may also contain a catalyst to catalyze a reaction of the analyte. The components of the sensing layer may be in a fluid or gel that is proximate to or in contact with the working electrode 58. Alternatively, the components of the sensing layer 64 may be disposed in a polymeric or sol-gel matrix that is proximate to or on the working electrode 58. In certain embodiments, the components of the sensing layer 64 are non-leachably disposed within the sensor 42 and in certain embodiments the components of the sensor 42 are immobilized within the sensor 42.

In addition to the electrodes 58, 60, 62 and the sensing layer 64, the sensor 42 may also include optional components such as one or more of the following: a temperature probe 66 (see for example FIGS. 5 and 7), a mass transport limiting layer 74, e.g., a matrix such as a membrane or the like, (see for example FIG. 8), a biocompatible layer 75 (see for example FIG. 8), and/or other optional components, as described below. Each of these items enhances the functioning of and/or results from the sensor 42, as discussed below.

The substrate 50 may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In addition to considerations regarding flexibility, it is often desirable that a sensor 42 should have a substrate 50 which is non-toxic. Preferably, the substrate 50 is approved by one or more appropriate governmental agencies or private groups for in vivo use. Although the substrate 50 in at least some embodiments has uniform dimensions along the entire length of the sensor 42, in other embodiments, the substrate 50 has a distal end 67 and a proximal end 65 with different widths 53, 55, respectively, as illustrated in FIG. 2.

At least one conductive trace 52 may be formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 50, as illustrated in FIG. 2, although this is not necessary. The conductive traces may be formed using a conductive material 56 such as carbon (e.g., graphite), a conductive polymer, a metal or alloy (e.g., gold or gold alloy), or a metallic compound (e.g., ruthenium dioxide or titanium dioxide), and the like. Conductive traces 52 (and channels 54, if used) may be formed with relatively narrow widths. In embodiments with two or more conductive traces 52 on the same side of the substrate 50, the conductive traces 52 are separated by distances sufficient to prevent conduction between the conductive traces 52. The working electrode 58 and the counter electrode 60 (if a separate reference electrode is used) may be made using a conductive material 56, including carbon.

The reference electrode 62 and/or counter/reference electrode may be formed using conductive material 56 that is a suitable reference material, for example silver/silver chloride or a non-leachable redox couple bound to a conductive material, for example, a carbon-bound redox couple. The electrical contact 49 may be made using the same material as the conductive material 56 of the conductive traces 52, or alternatively, may be made from a carbon or other non-metallic material, including a conducting polymer.

Figure 6:
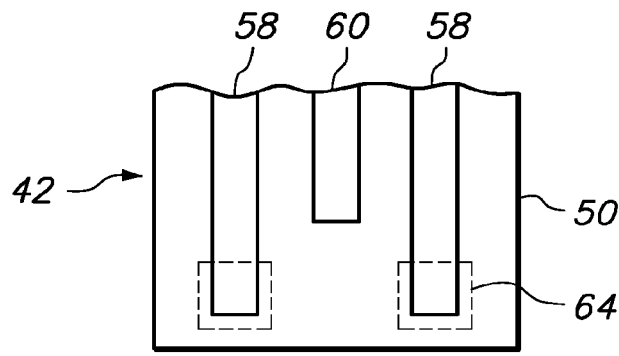
FIG. 6 is an expanded top view of a tip-portion of the analyte sensor of FIG. 6.
Figure 7:
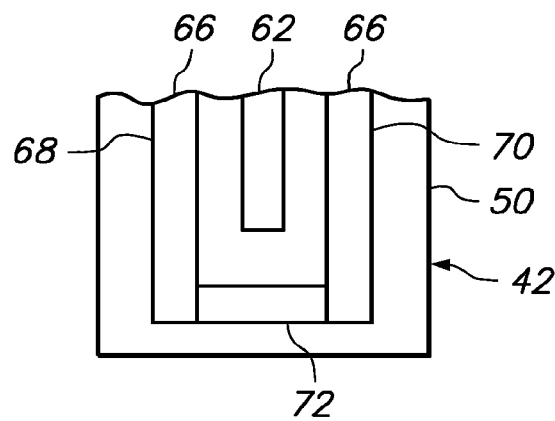
FIG. 7 is an expanded bottom view of a tip-portion of the analyte sensor of FIG. 6.

A number of exemplary electrode configurations are described below, however, it will be understood that other configurations may also be used. In certain embodiments, e.g., illustrated in FIG. 3A, the sensor 42 includes two working electrodes 58a, 58b and one counter electrode 60, which also functions as a reference electrode. In another embodiment, the sensor includes one working electrode 58a, one counter electrode 60, and one reference electrode 62, as shown for example in FIG. 3B. Each of these embodiments is illustrated with all of the electrodes formed on the same side of the substrate 50. Alternatively, one or more of the electrodes may be formed on an opposing side of the substrate 50. In another embodiment, two working electrodes 58 and one counter electrode 60 are formed on one side of the substrate 50 and one reference electrode 62 and a temperature probe 66 are formed on an opposing side of the substrate 50, for example as illustrated in FIG. 6. The opposing sides of the tip of this embodiment of the sensor 42 are illustrated in FIGS. 6 and 7.

Some analytes, such as oxygen, may be directly electrooxidized or electroreduced on the working electrode 58. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode 58. For these analytes, each working electrode 58 has a sensing layer 64 formed proximate to or on a working surface of the working electrode 58. In many embodiments, the sensing layer 64 is formed near or on only a small portion of the working electrode 58, e.g., near a tip of the sensor 42.

The sensing layer 64 includes one or more components designed to facilitate the electrolysis of the analyte. The sensing layer 64 may be formed as a solid composition of the desired components (e.g., an electron transfer agent and/or a catalyst). These components may be non-leachable from the sensor 42 and may be immobilized on the sensor 42. Examples of immobilized sensing layers are described in, e.g., U.S. Pat. Nos. 5,262,035; 5,264,104; 5,264,105; 5,320,725; 5,593,852; and 5,665,222; and PCT Patent Application No. US98/02403 entitled "Soybean Peroxidase Electrochemical Sensor".

Sensors having multiple working electrodes 58a may also be used, e.g., and the signals therefrom may be averaged or measurements generated at these working electrodes 58a may be averaged. In addition, multiple readings at a single working electrode 58a or at multiple working electrodes may be averaged.

Figure 3A:
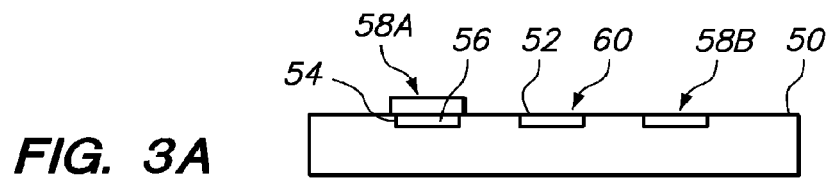
FIG. 3A is a cross-sectional view of the analyte sensor of FIG. 2.
Figure 3B:
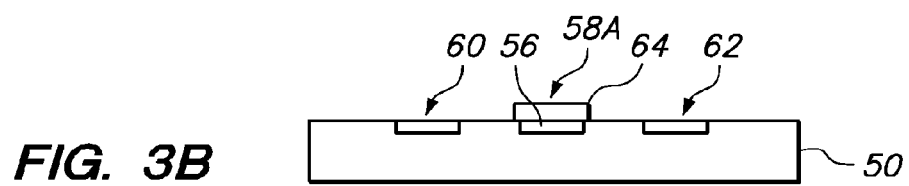
FIG. 3B is a cross-sectional view of another embodiment of an analyte sensor, according to the invention.

In many embodiments, the sensing layer 64 contains one or more electron transfer agents in contact with the conductive material 56 of the working electrode 58, as shown in FIGS. 3A and 3B. Useful electron transfer agents and methods for producing them are described in, e.g., U.S. Pat. Nos. 5,264,104; 5,356,786; 5,262,035; 5,320,725, 6,175, 752, and 6,329,161.

The sensing layer 64 may also include a catalyst which is capable of catalyzing a reaction of the analyte. The catalyst may also, in some embodiments, act as an electron transfer agent.

To electrolyze the analyte, a potential (versus a reference potential) is applied across the working and counter electrodes 58, 60. When a potential is applied between the working electrode 58 and the counter electrode 60, an electrical current will flow. Those skilled in the art will recognize that there are many different reactions that will achieve the same result; namely the electrolysis of an analyte or a compound whose level depends on the level of the analyte.

A variety of optional items may be included in the sensor. One optional item is a temperature probe 66 (see for example FIGS. 5 and 7). One exemplary temperature probe 66 is formed using two probe leads 68, 70 connected to each other through a temperature-dependent element 72 that is formed using a material with a temperature-dependent characteristic. An example of a suitable temperature-dependent characteristic is the resistance of the temperature-dependent element 72.

The temperature probe 66 may provide a temperature adjustment for the output from the working electrode 58 to offset the temperature dependence of the working electrode 58.

Figure 8:
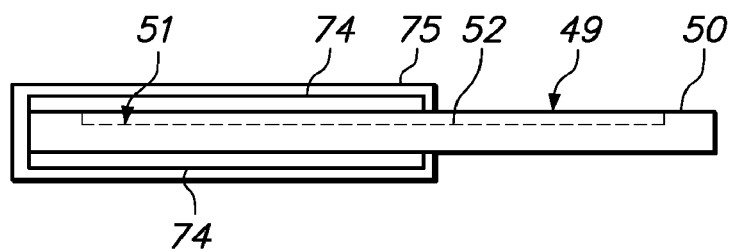
FIG. 8 is a side view of the analyte sensor of FIG. 2.

The sensors of the subject invention are biocompatible. Biocompatibility may be achieved in a number of different manners. For example, an optional biocompatible layer 74 may be formed over at least that portion of the sensor 42 which is inserted into the patient, for example as shown in FIG. 8.

An interferant-eliminating layer (not shown) may be included in the sensor 42. The interferant-eliminating layer may include ionic components, such as, for example, NAFION or the like, incorporated into a polymeric matrix to reduce the permeability of the interferant-eliminating layer to ionic interferants having the same charge as the ionic components.

A mass transport limiting layer 74 may be included with the sensor to act as a diffusion-limiting barrier to reduce the rate of mass transport of the analyte, for example, glucose or lactate, into the region around the working electrodes 58. Exemplary layers that may be used are described for example, in U.S. Pat. No. 6,881,551.

A sensor of the subject invention may be adapted to be a replaceable component in an in vivo analyte monitor, and particularly in an implantable analyte monitor. In many embodiments, the sensor is capable of operation over a period of days or more, e.g., a period of operation may be at least about one day, e.g., at least about three days, e.g., at least about one week or more. The sensor may then be removed and replaced with a new sensor.

Any suitable device may be used to insert a sensor of the subject invention into the patient (e.g., in the subcutaneous tissue or the like). Exemplary insertion devices that may be used are described for example, in U.S. Pat. No. 6,175,752.

In operation, a sensor is placed within or next to an insertion device and then a force is provided against the insertion device and/or sensor to carry the sensor 42 into the skin of the patient. The insertion device is optionally pulled out of the skin with the sensor remaining beneath the skin, e.g., in the subcutaneous tissue, due to frictional forces between the sensor and the patient's tissue.

In certain embodiments, the sensor is injected between about 2 to about 12 mm into the interstitial tissue of the patient for subcutaneous implantation. Other embodiments of the invention may include sensors implanted in other portions of the patient, including, for example, in an artery, vein, or organ. The depth of implantation varies depending on the desired implantation target.

Although a sensor of the subject invention may be inserted anywhere in the body, it is often desirable that the insertion site be positioned so that an on-skin sensor control unit 44 may be concealed. In addition, it is often desirable that the insertion site be at a place on the body with a low density of nerve endings to reduce the pain to the patient. Examples of sites for insertion of the sensor 42 and positioning of the on-skin sensor control unit 44 include but are not limited to the abdomen, thigh, leg, upper arm, and shoulder.

Figure 9:
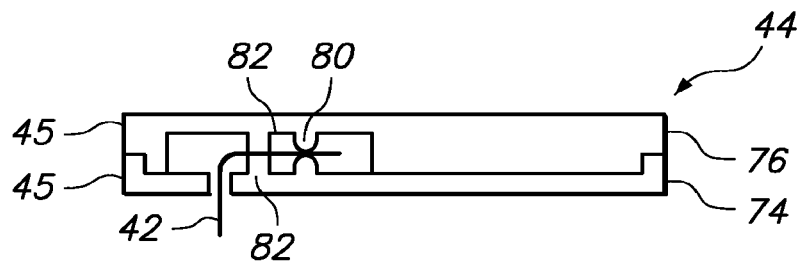
FIG. 9 is a cross-sectional view of an embodiment of an on-skin sensor control unit, according to the invention.
Figure 10:
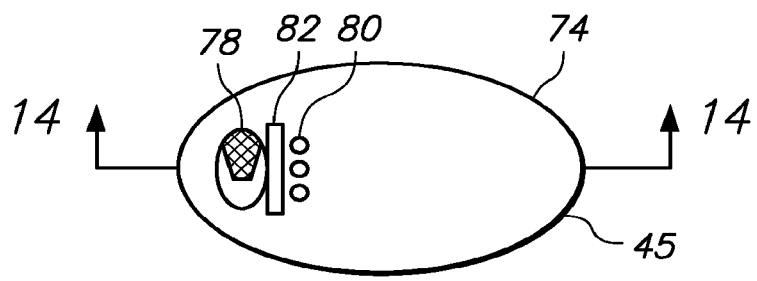
FIG. 10 is a top view of a base of the on-skin sensor control unit of FIG. 9.
Figure 11:
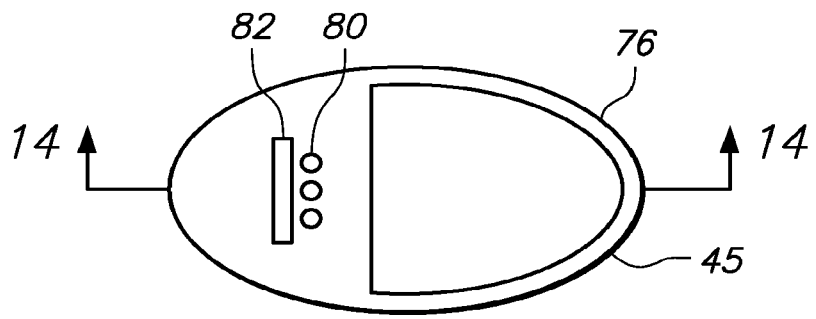
FIG. 11 is a bottom view of a cover of the on-skin sensor control unit of FIG. 9.
Figure 12:
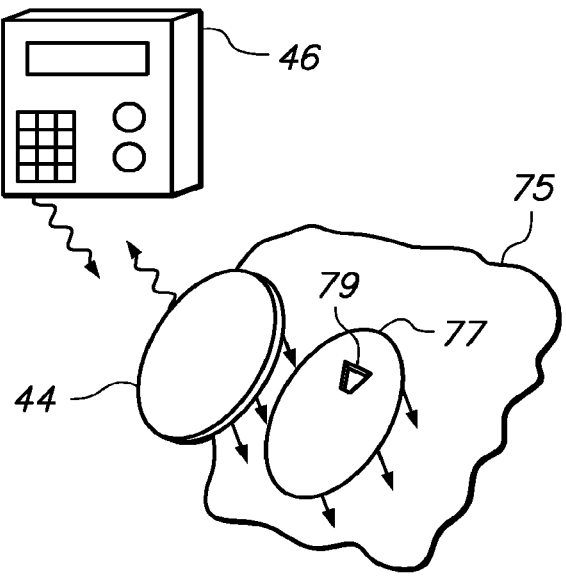
FIG. 12 is a perspective view of the on-skin sensor control unit of FIG. 9 on the skin of a patient.

The on-skin sensor control unit 44 is configured to be placed on the skin of a patient. One embodiment of the on-skin sensor control unit 44 has a thin, oval shape to enhance concealment, as illustrated in FIGS. 9-11. However, other shapes and sizes may be used. The on-skin sensor control unit 44 includes a housing 45, as illustrated in FIGS. 9-11. The on-skin sensor control unit 44 is typically attachable to the skin 75 of the patient, as illustrated in FIG. 12. Another method of attaching the housing 45 of the on-skin sensor control unit 44 to the skin 75 includes using a mounting unit 77 which includes an opening 79 through which the sensor 42 maybe inserted. Additional detailed description of the on-skin sensor control unit and 44 and the associated electronic components are provided for example, in U.S. Pat. No. 6,175,752.

The sensor 42 and the electronic components within the on-skin sensor control unit 44 are coupled via conductive contacts 80. The one or more working electrodes 58, counter electrode 60 (or counter/reference electrode), optional reference electrode 62, and optional temperature probe 66 are attached to individual conductive contacts 80. In the illustrated embodiment of FIGS. 9-11, the conductive contacts 80 are provided on the interior of the on-skin sensor control unit 44.

Figure 13A:
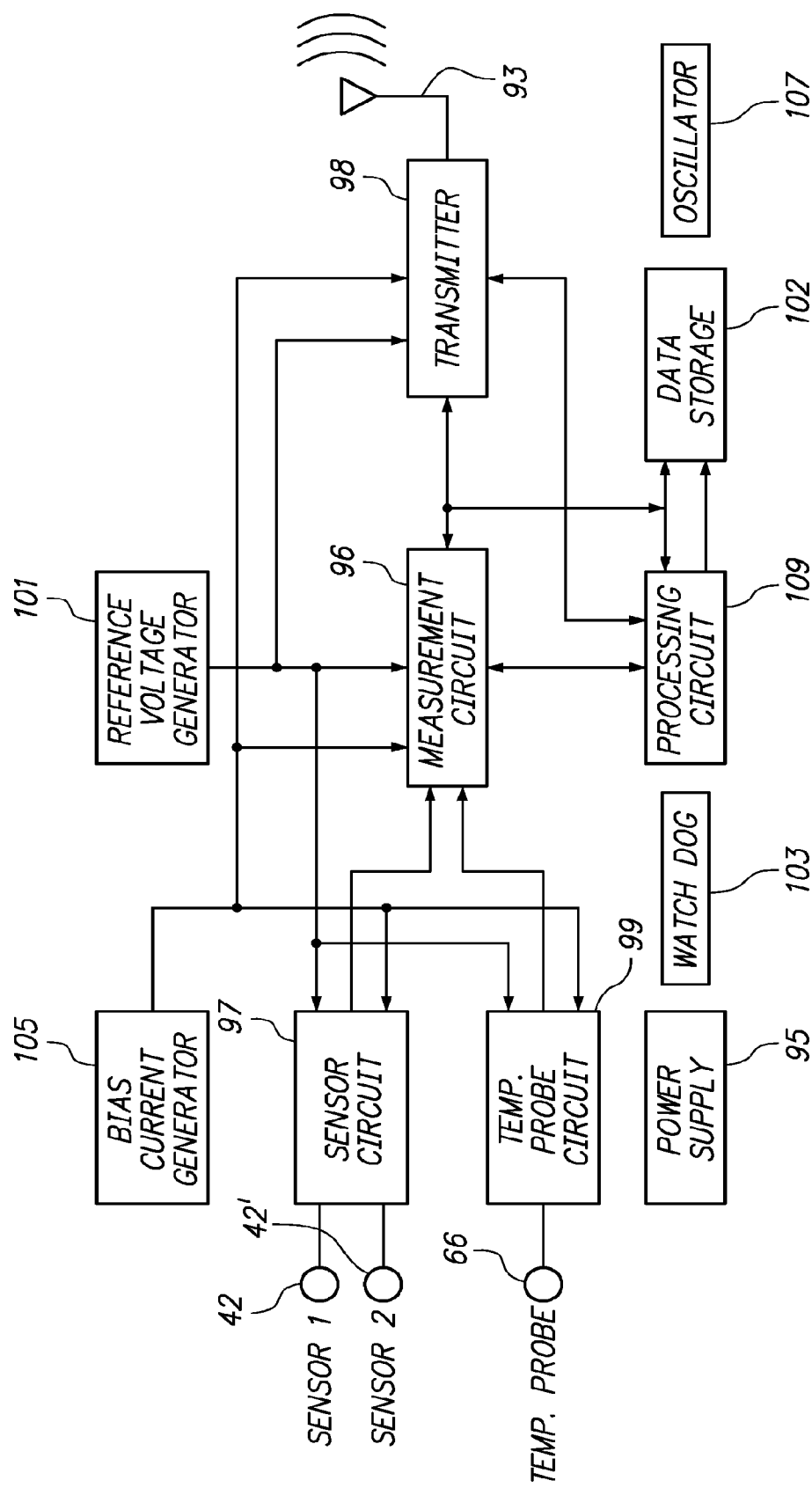
FIG. 13A is a block diagram of one embodiment of an on-skin sensor control unit, according to the invention.

The on-skin sensor control unit 44 may include at least a portion of the electronic components that operate the sensor 42 and the analyte monitoring device system 40. One embodiment of the electronics in the on-skin control unit 44 is illustrated as a block diagram in FIG. 13A. The electronic components of the on-skin sensor control unit 44 may include a power supply 95 for operating the on-skin control unit 44 and the sensor 42, a sensor circuit 97 for obtaining signals from and operating the sensor 42, a measurement circuit 96 that converts sensor signals to a desired format, and a processing circuit 109 that, at minimum, obtains signals from the sensor circuit 97 and/or measurement circuit 96 and provides the signals to an optional transmitter 98. In some embodiments, the processing circuit 109 may also partially or completely evaluate the signals from the sensor 42 and convey the resulting data to the optional transmitter 98 and/or activate an optional alarm system 94 (see for example FIG. 13B) if the analyte level exceeds a threshold. The processing circuit 109 often includes digital logic circuitry.

The on-skin sensor control unit 44 may optionally contain a transmitter or transceiver 98 for transmitting the sensor signals or processed data from the processing circuit 109 to a receiver (or transceiver)/display unit 46, 48; a data storage unit 102 for temporarily or permanently storing data from the processing circuit 109; a temperature probe circuit 99 for receiving signals from and operating a temperature probe 66; a reference voltage generator 101 for providing a reference voltage for comparison with sensor-generated signals; and/or a watchdog circuit 103 that monitors the operation of the electronic components in the on-skin sensor control unit 44. Moreover, the sensor control unit 44 may include a bias control generator 105 to correctly bias analog and digital semiconductor devices, an oscillator 107 to provide a clock signal, and a digital logic and timing component 109 to provide timing signals and logic operations for the digital components of the circuit.

Figure 13B:
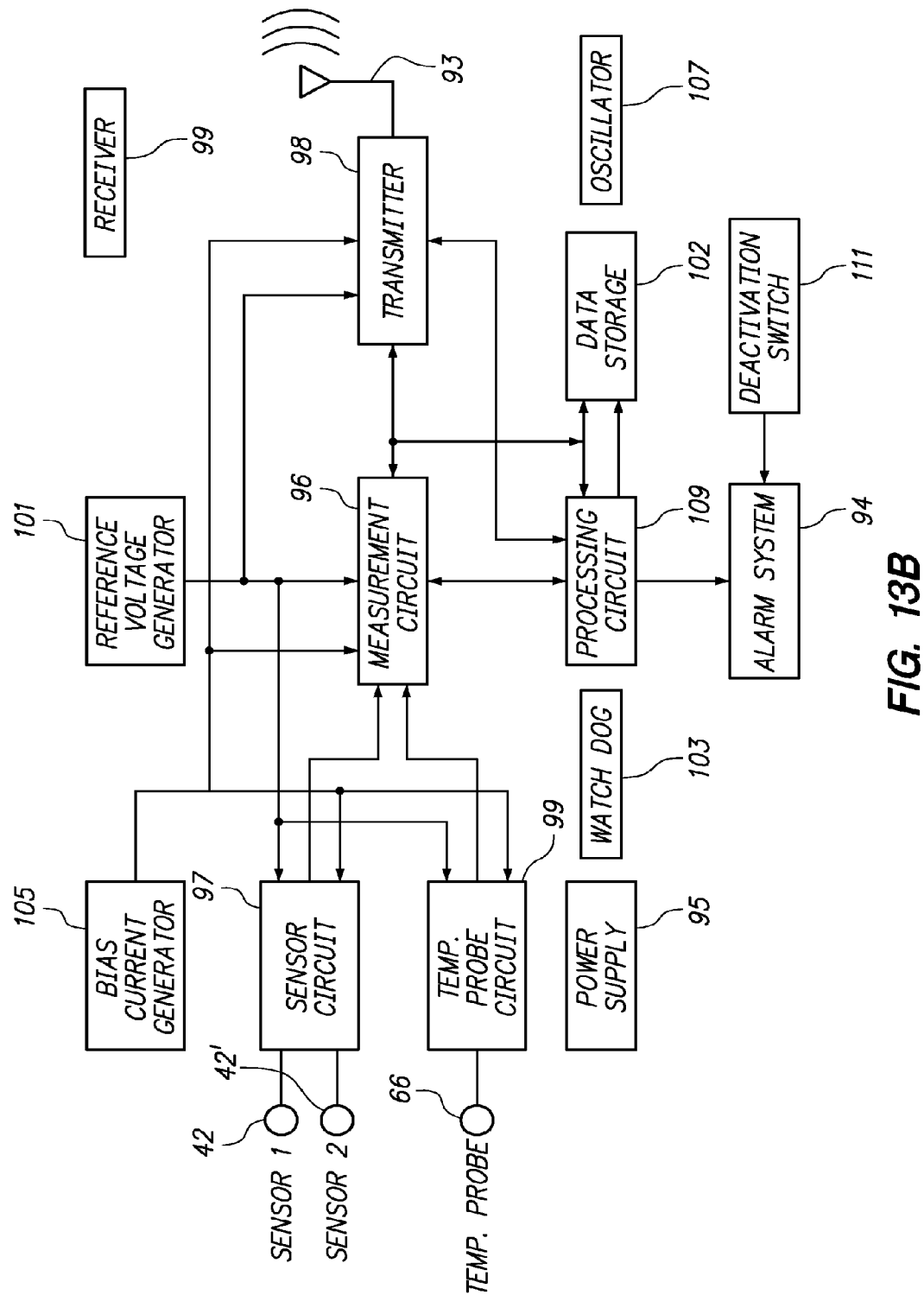
FIG. 13B is a block diagram of another embodiment of an on-skin sensor control unit, according to the invention.

FIG. 13B illustrates a block diagram of another exemplary on-skin control unit 44 that also includes optional components such as a receiver (or transceiver) 99 to receive, for example, calibration data; a calibration storage unit 100 to hold, for example, factory-set calibration data, calibration data obtained via the receiver 99 and/or operational signals received, for example, from a receiver/display unit 46, 48 or other external device; an alarm system 104 for warning the patient; and a deactivation switch 111 to turn off the alarm system.

Functions of the analyte monitoring system 40 and the sensor control unit 44 may be implemented using either software routines, hardware components, or combinations thereof. The hardware components may be implemented using a variety of technologies, including, for example, integrated circuits or discrete electronic components. The use of integrated circuits typically reduces the size of the electronics, which in turn may result in a smaller on-skin sensor control unit 44.

The electronics in the on-skin sensor control unit 44 and the sensor 42 are operated using a power supply 95. The sensor control unit 44 may also optionally include a temperature probe circuit 99.

The output from the sensor circuit 97 and optional temperature probe circuit is coupled into a measurement circuit 96 that obtains signals from the sensor circuit 97 and optional temperature probe circuit 99 and, at least in some embodiments, provides output data in a form that, for example can be read by digital circuits.

In some embodiments, the data from the processing circuit 109 is analyzed and directed to an alarm system 94 (see for example FIG. 13B) to warn the user.

In some embodiments, the data (e.g., a current signal, a converted voltage or frequency signal, or fully or partially analyzed data) from processing circuit 109 is transmitted to one or more receiver/display units 46, 48 using a transmitter 98 in the on-skin sensor control unit 44. The transmitter has an antenna 93 formed in the housing 45.

In addition to a transmitter 98, an optional receiver 99 may be included in the on-skin sensor control unit 44 or elsewhere. In some cases, the transmitter 98 is a transceiver, operating as both a transmitter and a receiver. The receiver 99 (and/or receiver display/units 46, 48) may be used to receive calibration data for the sensor 42. The calibration data may be used by the processing circuit 109 to correct signals from the sensor 42. This calibration data may be transmitted by the receiver/display unit 46, 48 or from some other source such as a control unit in a doctor's office.

Calibration data may be obtained in a variety of ways. For instance, the calibration data may simply be factory-determined calibration measurements which may be input into the on-skin sensor control unit 44 using the receiver 99 or may alternatively be stored in a calibration data storage unit 100 within the on-skin sensor control unit 44 itself or elsewhere such as, e.g., receiver display/units 46, 48, (in which case a receiver 99 may not be needed). The calibration data storage unit 100 may be, for example, a readable or readable/writeable memory circuit.

Alternative or additional calibration data may be provided based on tests performed by a doctor or some other professional or by the patient himself. For example, it is common for diabetic individuals to determine their own blood glucose concentration using commercially available testing kits. The result of this test is input into the on-skin sensor control unit 44 (and/or receiver display/units 46, 48) either directly, if an appropriate input device (e.g., a keypad, an optical signal receiver, or a port for connection to a keypad or computer) is incorporated in the on-skin sensor control unit 44, or indirectly by inputting the calibration data into the receiver/display unit 46, 48 and transmitting the calibration data to the on-skin sensor control unit 44.

Other methods of independently determining analyte levels may also be used to obtain calibration data. This type of calibration data may supplant or supplement factory-determined calibration values.

In some embodiments of the invention, calibration data may be required at periodic intervals, for example, about every ten hours, or about eight hours, about once a day, or about once a week, to confirm that accurate analyte levels are being reported. Calibration may also be required each time a new sensor 42 is implanted or if the sensor exceeds a threshold minimum or maximum value or if the rate of change in the sensor signal exceeds a threshold value. In some cases, it may be necessary to wait a period of time after the implantation of the sensor 42 before calibrating to allow the sensor 42 to achieve equilibrium. In some embodiments, the sensor 42 is calibrated only after it has been inserted. In other embodiments, no calibration of the sensor 42 is needed (e.g., a factory calibration may be sufficient).

Regardless of the type of analyte monitoring system employed, it has been observed that transient, low readings may occur for a period of time. These anomalous low readings may occur during the first hours of use, or anytime thereafter. In certain embodiments, spurious low readings may occur during the night and may be referred to as "night time dropouts". For example, in the context of an operably positioned continuous monitoring analyte sensor under the skin of a user, such spurious low readings may occur for a period of time following sensor positioning and/or during the first night post-positioning. In many instances, the low readings resolve after a period of time. However, these transient, low readings put constraints analyte monitoring during the low reading period. Attempts to address this problem vary and include delaying calibration and/or reporting readings to the user until after this period of low readings passes after positioning of the sensor or frequent calibration of the sensor-both of which are inconvenient and neither of which is desirable.

However, as noted above embodiments of the subject invention have at least a minimal period, if at all, of spurious low readings, i.e., a substantially reduced sensor equilibration period, including substantially no equilibration period. In this regard, in those embodiments in which an initial post-positioning calibration is required, such may be performed substantially immediately after sensor positioning. For example, in certain embodiments a calibration protocol may include a first post-positioning calibration at less than about 10 hours after a sensor has been operably positioned, e.g., at less than about 5 hours, e.g., at less than about 3 hours, e.g., at less than about 1 hour, e.g., at less than about 0.5 hours. One or more additional calibrations may not be required, or may be performed at suitable times thereafter.

The on-skin sensor control unit 44 may include an optional data storage unit 102 which may be used to hold data (e.g., measurements from the sensor or processed data).

In some embodiments of the invention, the analyte monitoring device 40 includes only an on-skin control unit 44 and a sensor 42.

Figure 14:
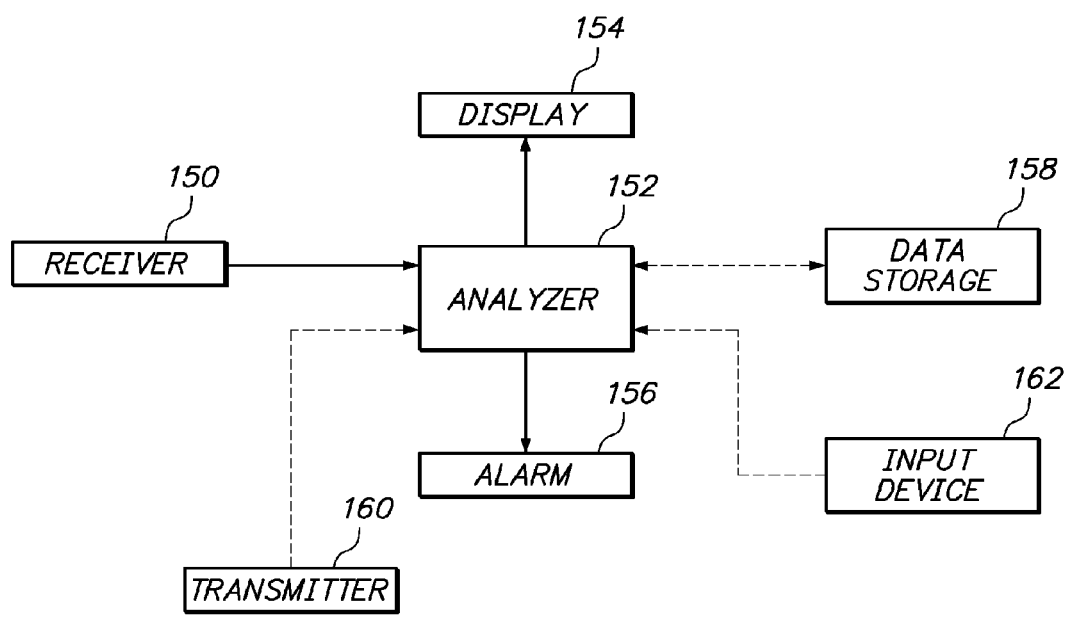
FIG. 14 is a block diagram of one embodiment of a receiver/display unit, according to the invention.

Referring back to FIG. 1, one or more receiver/display units 46, 48 may be provided with the analyte monitoring device 40 for easy access to the data generated by the sensor 42 and may, in some embodiments, process the signals from the on-skin sensor control unit 44 to determine the concentration or level of analyte in the subcutaneous tissue. As shown in FIG. 14, the receiver/display units 46, 48, typically include a receiver 150 to receive data from the on-skin sensor control unit 44, an analyzer 152 to evaluate the data, a display 154 to provide information to the patient, and an alarm system 156 to warn the patient when a condition arises. The receiver/display units 46, 48 may also optionally include a data storage device 158, a transmitter 160, and/or an input device 162.

Data received by the receiver 150 is then sent to an analyzer 152. The output from the analyzer 152 is typically provided to a display 154. The receiver/display units 46, 48 may also include a number of optional items such as a data storage unit 158 to store data, a transmitter 160 which can be used to transmit data, an input device 162, such as a keypad or keyboard. The receiver/display units 46, 48 may be a compact handheld unit and also include a transceiver. In certain embodiments, the receiver/display unit 46, 48 is integrated with a calibration unit (not shown) and may include a conventional blood glucose meter.

In certain embodiments, analyte data (processed or not) may be forwarded (such as by communication) to a remote location such as a doctor's office if desired, and received there for further use (such as further processing).

Integration with a Drug Administration System

The subject invention also includes sensors including an antiglycolytic agent and a chelating agent, which sensors are used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, an on-skin sensor control unit, a receiver/display unit, a data storage and controller module, and a drug administration system. In some cases, the receiver/display unit, data storage and controller module, and drug administration system may be integrated in a single unit. The sensor-based drug delivery system uses data form the one or more sensors to provide necessary input for a control algorithm/mechanism in the data storage and controller module to adjust the administration of drugs. As an example, a glucose sensor could be used to control and adjust the administration of insulin.

Finally, kits for use in practicing the subject invention are also provided. The subject kits may include an antiglycolytic agent or precursor thereof in any suitable form as described herein. For example, a kit may include one or more antiglycolytic sensors as described herein, and/or other structure that includes an antiglycolytic agent or precursor thereof. In certain embodiments, a kit may include an antiglycolytic agent or precursor thereof adapted for transdermal or parenteral administration. Embodiments may also include a sensor insertion device and/or transmitter and/or receiver.

In addition to one or more sensors, the subject kits may also include written instructions for using a sensor. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

In many embodiments of the subject kits, the components of the kit are packaged in a kit containment element to make a single, easily handled unit, where the kit containment element, e.g., box or analogous structure, may or may not be an airtight container, e.g., to further preserve the one or more sensors and additional reagents (e.g., control solutions), if present, until use.

The following examples are offered by way of illustration and not by way of limitation.

Experimental

The following examples are put forth so as to provide those of ordinary skill in the art with a complete disclosure and description of how to make and use the embodiments of the invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following experiments demonstrate that blood glucose concentrations can be substantially lowered in the vicinity of blood clots and further that sensors that include antiglycolytic agents can delay and/or reduce the lowering so that such sensors do not exhibit the period of low reading observed with sensors that do not include an antiglycolytic agent. In this manner, it is demonstrated that clinically accurate analyte readings may be obtained from such sensors substantially immediately after inserting the sensor.

FIGS. 15A, 15B, 15C and 15D show the experimental set-up for measuring glucose levels using platelet-rich plasma, heparinized whole blood, and non heparinized whole blood, respectively.

Figure 15A:
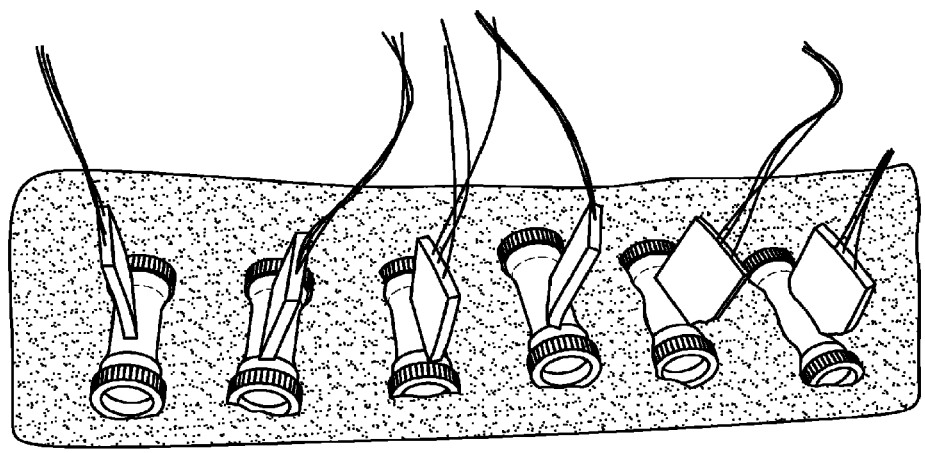
FIG. 15A shows an experimental set-up that includes analyte sensors in biofluid-containing tubes.
Figure 15B:
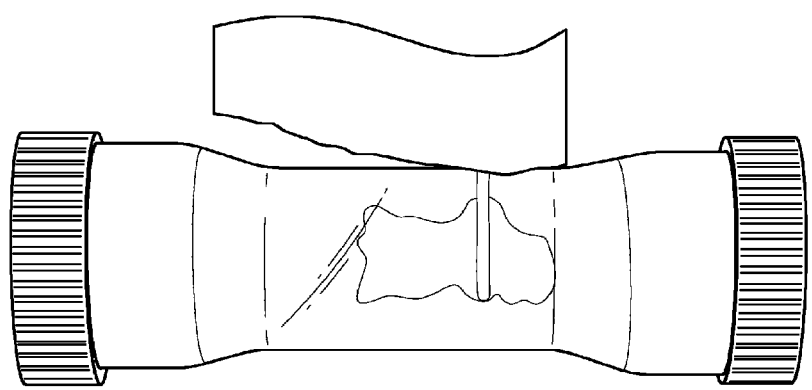
FIG. 15B shows a sensor in a plasma-containing tube.
Figure 15C:
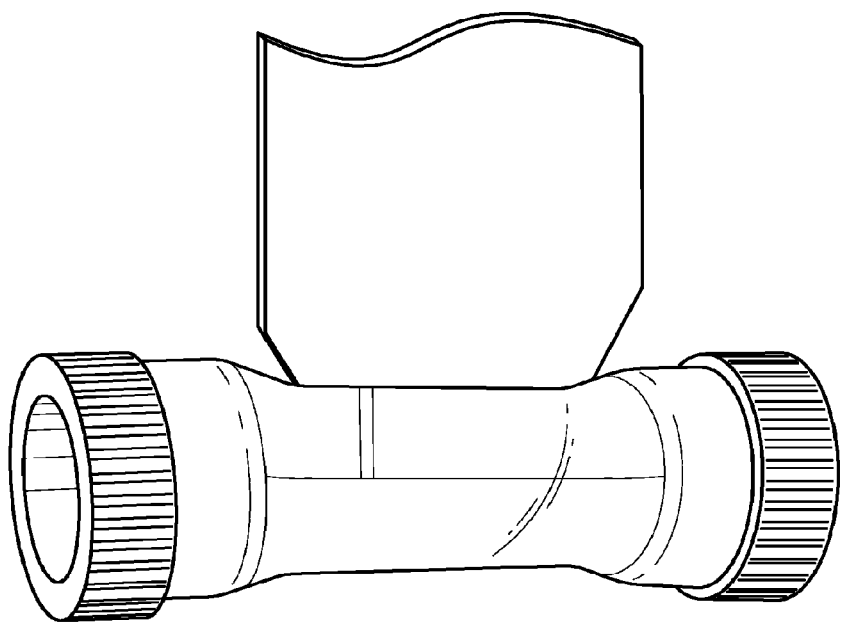
FIG. 15C shows a sensor in a heparinized whole blood-containing tube.
Figure 15D:
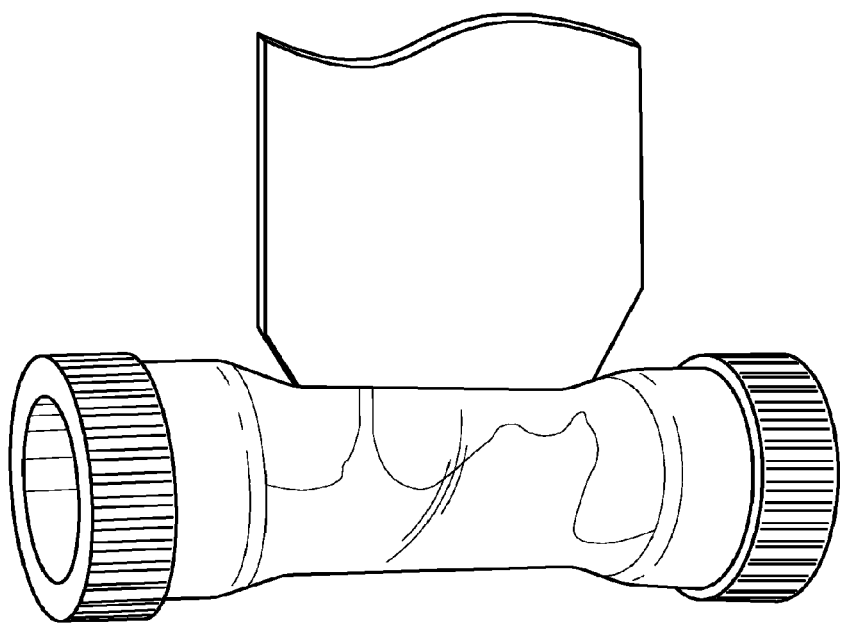
FIG. 15D shows a sensor is a non heparinized whole blood containing tube.

Glucose sensors are inserted into small silicon tubes containing the appropriate biological fluid. The tubes are maintained at about 37 degrees Celsius, and the glucose sensor is monitored. FIG. 15D shows the formation of a blood clot around the sensor.

Figure 15E:
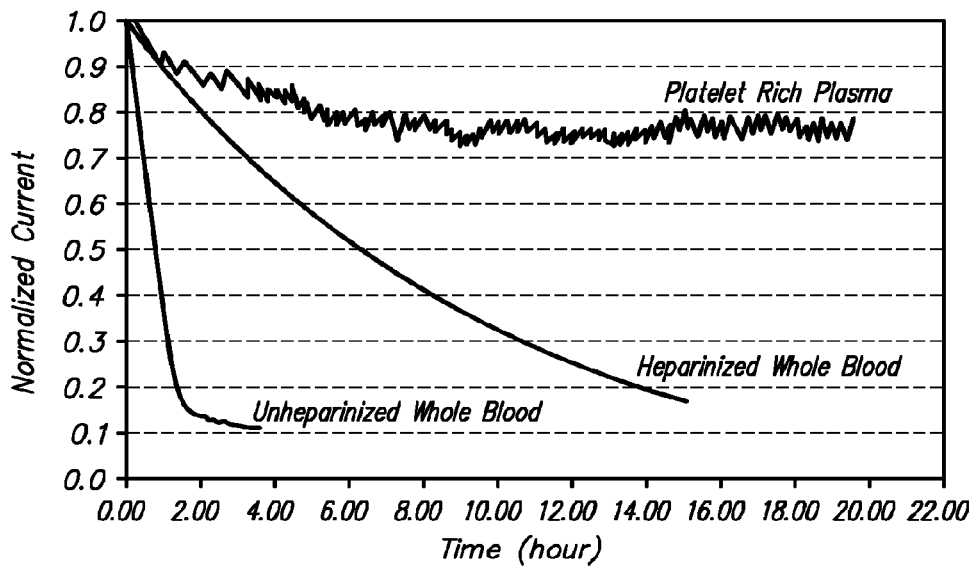
FIG. 15E shows a graph of sensor readings according to the experimental conditions.

As shown in FIG. 15E, the platelet-rich plasma shows a nearly constant glucose response, consistent with the lack of glucose-consuming red cells. The heparinized (non clotted) blood shows depletion over about a 15 hour period, consistent with rates of glycolysis in anticoagulant-containing blood. The clotted blood shows a much more rapid depletion (within about 1.5-2 hours), consistent with localized depletion by the highly concentrated red cells in the clot surrounding the sensor.

In the case of the clot, simple obstruction of the sensor surface by an impermeable clot is ruled out as a source of glucose depletion because the depletion rate (as a percentage of total current) varies with glucose concentration. High glucose samples take longer to deplete than lower glucose samples. This is consistent with active consumption of glucose by the surrounding clot.

Figure 16:
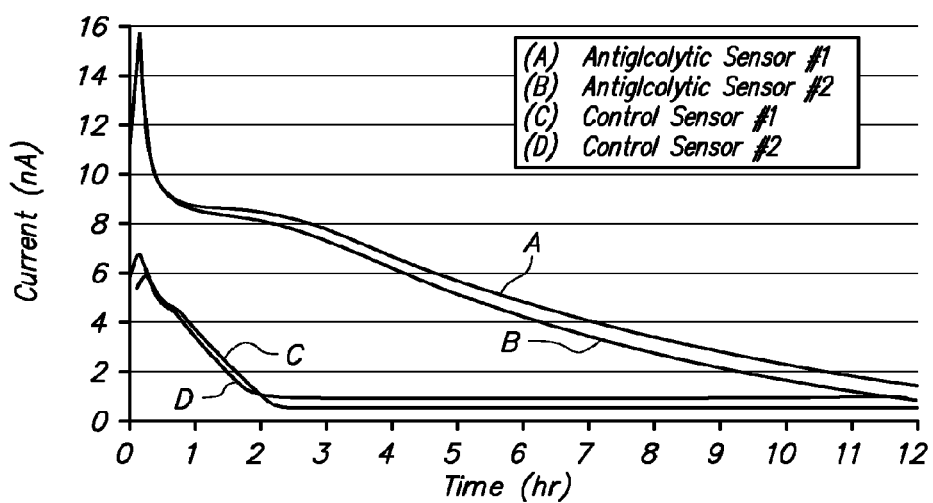
FIG. 16 shows a graph of sensor readings of antiglycolytic sensors and control sensors.

FIG. 16 shows that even modest amounts of an antiglycolytic agent, included into a glucose sensor, can greatly retard, if not minimize, glucose consumption by a blood clot which surrounds the sensor. Antiglycolytic sensors were prepared by modification of control sensors (FREESTYLE NAVIGATOR®) as follows. A coating solution was prepared from 250 mg/mL of a racemic mixture of L-glyceraldehyde and D-glyceraldehyde, and 150 mg/mL in polymer PC-1306 (Biocompatibles, PLC), the former suspended and the latter dissolved in ethanol. The resulting antiglycolytic sensors had approximately 138 micrograms of the racemic mixture of D- and L-glyceraldehydes incorporated as a thin, outer coating. Both these sensors and control sensors (no antiglycolytic agents added) were then inserted into blood clots, and the current response was followed over time.

As the graph of FIG. 16 shows, the control sensors show the previously-observed about 2 hour glucose depletion period. The depletion is much delayed (up to about 12 hours) in the glyceraldehydes-containing sensors. This demonstrates that the glyceraldehydes are being incorporated into the red cells adjacent to the sensor, and are reducing glucose consumption by the adjacent red blood cells.

A further example of the use of an antiglycolytic sensor is provided by its use in an in vivo environment. In this example, a control sensor (FREESTYLE NAVIGATOR®) is inserted in the arm of a non-diabetic subject, adjacent to a similar sensor, which has been modified by the addition of an antiglycolytic agent, L-glyceraldehyde. A coating solution was made 200 mg/mL in L-glyceraldehyde, and 150 mg/mL in polymer PC-1306 (Biocompatibles, PLC), both dissolved in ethanol. The FREESTYLE NAVIGATOR® sensor was then modified by dipping twice into this coating solution, yielding an overcoat containing about 55 micrograms of L-glyceraldehyde.

Figure 17:
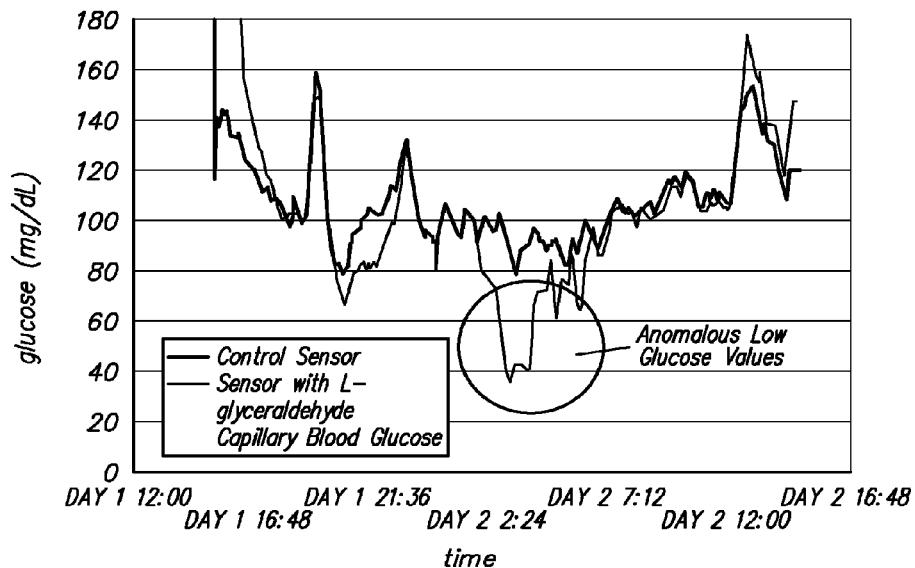
FIG. 17 shows a comparison of an antiglycolytic sensor and a control sensor in vivo.

FIG. 17 shows the performance of these two sensors, implanted side by side in the arm of a non-diabetic subject. Note that the control sensor shows a large negative deviation (to values well below 60 mg/dL) in signal during the night, while the antiglycolytic-modified sensor does not. Glucose readings below 60 mg/dL are not anticipated in non-diabetic subjects, and are therefore considered to be anomalous, reflecting either (a) sensor malfunctions, or more likely (b) local inhomogeneities of glucose concentration (in the vicinity of a wound, for example) wherein the glucose concentration deviates substantially from the systemic value. Such deviations are observed with some regularity in control sensors, but are not observed in sensors modified with L-glyceraldehyde.

Figure 18:
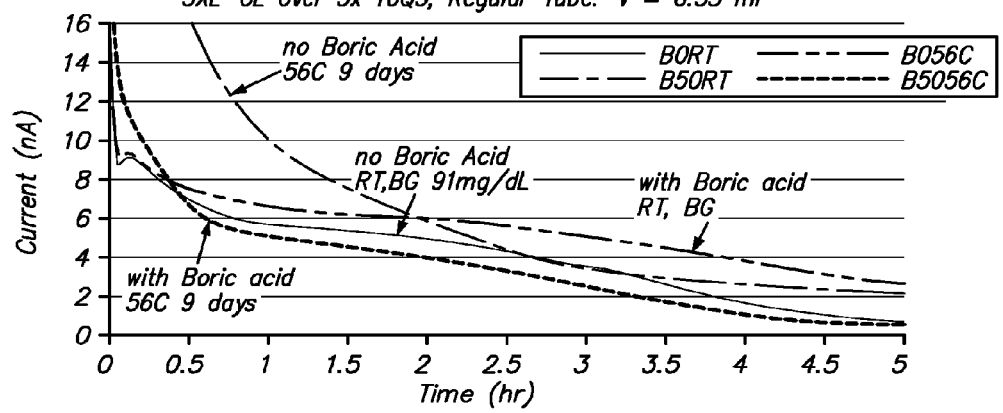
FIG. 18 shows the effect of stress on glucose biosensors with and without the addition of boric acid. Boric acid and L-glyceraldehyde are incorporated into the outer membrane of the biosensors. The high background current is significantly reduced when boric acid is added to the membrane formulation.

An example of the use of an antiglycolytic sensor containing borate minerals, boric acid or any precursor thereof, is provided by its testing in an in vitro environment. 50 mg/ml boric acid was mixed with 150 mg/ml L-glyceraldehyde and 150 mg/mL PC in 100% ethanol. The sensor was dipped three times with a 10 minute interval. The sensor was then cured overnight, and subjected to stress at 56° C. for nine days and subsequently tested in nonheparin blood. FIG. 18 shows that the high background current is reduced significantly by adding borate to the formulation.

It is evident from the above results and discussion that the above-described invention provides devices and methods for continuous analyte monitoring. The above-described invention provides a number of advantages some of which are described above and which include, but are not limited to, the ability to provide clinically accurate analyte data without a substantial time delay after operably positioning the sensor in a patient or frequent calibrations. As such, the subject invention represents a significant contribution to the art.

While embodiments of the invention have been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for monitoring levels of glucose in a subject, the method comprising:
   determining over a period of time substantially immediately clinically accurate levels of glucose from signals generated by a glucose sensor after the glucose sensor is positioned into skin of a subject at an analyte determination site, the glucose sensor comprising:
      a working electrode comprising a sensing layer disposed thereon, the sensing layer comprising a glucose responsive enzyme,
      a membrane comprising at least one active agent comprising an antiglycolytic agent or precursor, the membrane disposed over at least a portion of the sensing layer, and
      a counter electrode,
         wherein the at least one active agent comprising the antiglycolytic agent or precursor thereof contacts the analyte determination site.

2. The method according to claim 1, wherein a Clark Error Grid is used to determine the clinically accurate levels of glucose from signals generated by the glucose sensor.

3. The method according to claim 1, wherein a MARD analysis is used to determine the clinically accurate levels of glucose from signals generated by the glucose sensor.

4. The method according to claim 1, wherein a Parks Error Grid is used to determine the clinically accurate levels of glucose from signals generated by the glucose sensor.

5. The method according to claim 1, wherein a Continuous Glucose Error Grid is used to determine the clinically accurate levels as of glucose from signals generated by the glucose sensor.

6. The method according to claim 1, wherein the clinically accurate levels of glucose from the signals generated by the glucose sensor are determined automatically.

7. The method according to claim 1, wherein clinically accurate levels of glucose from the signals generated by the sensor are determined continuously.

8. The method according to claim 1, wherein clinically accurate levels of glucose from the signals generated by the glucose sensor are determined periodically.

9. The method according to claim 1, wherein the period of time is one hour.

10. The method according to claim 1, wherein the period of time is three days or more.

11. The method according to claim 1, wherein the period of time is greater than one week.

12. The method according to claim 1, wherein the glucose sensor is positioned into the skin of the subject after one calibration of the glucose sensor.

13. The method according to claim 1, wherein the glucose sensor is positioned into the skin of the subject without calibrating the glucose sensor.

14. The method according to claim 1, wherein determining the clinically accurate levels of glucose from the signals generated by the glucose sensor comprises observing no spurious glucose measurements.

15. The method according to claim 1, wherein the sensing layer further comprises an electron transfer agent.

16. The method according to claim 15, wherein the glucose responsive enzyme and electron transfer agent are bonded to the sensing layer.

17. The method according to claim 1, wherein the glucose sensor further comprises one of:
   an interferent-eliminating layer; and
   a biocompatible layer.

18. The method according to claim 1, wherein the membrane is a mass transfer limiting membrane.

19. The method according to claim 1, wherein the glucose sensor is integrated with a drug delivery system and, further comprising, administering a drug based on the signals generated by the glucose sensor.

* * * * *